Figure 1:

United States Patent [19]

Lussi et al.

[11] Patent Number: 5,167,961
[45] Date of Patent: Dec. 1, 1992

[54] PROCESS FOR PREPARING HIGH PURITY BONE MINERAL

[75] Inventors: Heinz Lussi, Chur; Peter Geistlich, Stansstad, both of Switzerland

[73] Assignee: Ed. Geistlich Sohne AG Fur Chemische Industrie, Lucerne, Switzerland

[21] Appl. No.: 460,177

[22] PCT Filed: Jun. 2, 1989

[86] PCT No.: PCT/GB89/00618
§ 371 Date: Apr. 2, 1990
§ 102(e) Date: Apr. 2, 1990

[87] PCT Pub. No.: WO89/11880
PCT Pub. Date: Dec. 14, 1989

[30] Foreign Application Priority Data

Jun. 2, 1988 [GB] United Kingdom ............. 8813033

[51] Int. Cl.$^5$ .............. A61K 9/14; A61K 47/42; A61K 37/12; A61K 2/28
[52] U.S. Cl. ................. 424/423; 424/422; 424/484; 514/774; 530/350; 530/353; 530/840; 623/16
[58] Field of Search ......... 424/422, 423, 484, 549; 514/774; 530/350, 353, 840; 623/16

[56] References Cited

U.S. PATENT DOCUMENTS

| | | | |
|---|---|---|---|
| 2,968,593 | 1/1961 | Rapkin | 424/549 |
| 4,314,380 | 2/1982 | Miyata et al. | 623/16 |
| 4,434,094 | 2/1984 | Seyedin et al. | 530/416 |
| 4,455,256 | 6/1984 | Urist | 530/350 |
| 4,587,268 | 5/1986 | Pfirrmann | 514/774 |
| 4,654,464 | 3/1987 | Mittelmeier et al. | 623/16 |

FOREIGN PATENT DOCUMENTS 147021  7/1985 European Pat. Off. .
WO867265 12/1986 World Int. Prop. O. .
8901347  2/1989 World Int. Prop. O. .

OTHER PUBLICATIONS

Stegemann, et al. "Uber die anorganische Knochensubstanz nach Formamidaufschluss", Bd. 320 (1960) 272.
Skinner, et al., Calc. Tiss. Res. 10 (1972) 257.
Williams, et al., Science 119 (1954) 771.
Losse, et al., Nature 177 (1956) 1032.
Hurley, et al., Military Medicine (1957) 101.
Kershaw, The Pharmaceutical Journal 190 (1963) 537.
International Search Report (WO 86/07265).
International Search Report (WO 89/01347).
Partial European Search Report (EPA 147,021).
Solomons, T. W. Graham, Organic Chemistry, 2nd Ed. 1980.

*Primary Examiner*—Thurman K. Page
*Assistant Examiner*—Carlos Azpuru
*Attorney, Agent, or Firm*—Rothwell, Figg, Ernst & Kurz

[57] ABSTRACT

The invention provides a process for the preparation of high purity bone mineral wherein the organic matter is degraded by heating with ammonia or a primary amine, characterized in that the solubilized degradation products are extracted by washing with flowing water at temperature below 60° C., such heating with primary amine and washing steps optionally being repeated, whereby substantially all organic matter removable by these steps is removed, the bone mineral so treated being heated in air at temperatures between 250° C. and 600° C.

5 Claims, 1 Drawing Sheet

PROCESS FOR PREPARING HIGH PURITY BONE MINERAL

This invention relates to bone mineral products of large specific surface area.

Bones from slaughtered animals are an inexpensive raw material available in large quantities. They contain 50 to 60% of very fine crystallites of a form of hydroxylapatite bonded by collagenic tissue and containing significant qualities of proteinaceous and other matter as well as associated fat and muscle tissues. Such a hydroxylapatite, if it could be isolated in a pure state without changing its essential crystal structure, would represent a highly biocompatible remodelling bone implant material.

Natural bone mineral comprises hydroxyapatitelike crystallites with a particular degree of crystallinity, habit and size (irregular platelike morphology, 5-10nm in thickness 10-50 nm in length) and surface chemistry resulting from the calcium to phosphate ratio (37.5-38.0% calcium and 15.5-5-19.0% phosphorus). The inorganic phase of bone contains porosity including ultrastructural interstices (10-100 nm) between the crystallites occurring naturally and produced by removal of the organic phase, and microscopic spaces (1-20 microns) including osteocyte lacunae, canaliculi, vascular channels, volkman's canals, and the canals of haversian systems (100-500 nm). The specific surface area, which is a measure of porosity is in the range 50 to 100 $m^2/gm$ as determined by mercury porosimetry. The crystallinity of bone mineral can be characterized by X-ray diffraction and the porosity and crystallite morphology and size by electron microscopy. We have found that the composition and structure of natural bone mineral cannot be duplicated by calcium phosphate products formed in vitro or by naturally occurring hydroxyapatites prepared previously.

Hitherto two methods for the purification of natural bone mineral have been proposed namely calcination and solvent extraction.

The temperatures needed during calcination for the incineration of the organic constituents of the bones are rather high. This leads to extensive recrystallization of the mineral part with formation of much coarser crystals The so formed material exhibits a small specific surface and is not superior to any chemically precipitated hydroxylapatite.

It should be emphasized that bone mineral which has been subjected to a treatment which results in significant increase in crystal size is much less readily remodelled on implantation since osteoclasts and osteoblasts cannot readily perform on such large crystals the dual function of mineral resorption and generation of new bone. Such implanted inserts may thus remain unchanged indefinitely eventually giving rise to undesirable effects. On the other hand, many synthetic tricalcium phosphate products tend to be resorbed too rapidly for osteoblasts to regenerate new bone.

In the prior extraction process the proteins are extracted from degreased bone with a suitable solvent. The resulting bone mineral is then washed to remove the solvent.

Stegemann and Jung (Hoppe Seyler's Z. physiol. Chem. 320 (196) 272) used formamide for the protein extraction. This method proved to be impractical, the solvent being unstable under the conditions of hot extraction.

The sometimes recommended extraction with hot water instead of water washing after extraction was found to promote undesirable crystal growth (Skinner, Kempur and Pak: Calf. Tiss. Res. 10 (1972) 257).

The generally preferred method according to the prior art consists of the extraction of degreased bone with boiling ethylene diamine followed by washing with water. This method has been introduced by Willia's[and Irvine Jnr. (Science 119 (1954) 771) and later used by Losse and Hurley (Nature 177 (1956) 1032; Military Medicine (1957) 101) and by Kershaw (The Pharmaceutical Journal 190 (1963) 537). A patent for this process has been granted to Armour & Co. (U.S. Pat. No. 2,968,593 (1961)).

It has generally been claimed that extraction with ethylenediamine yields pure bone mineral. However, on repetition of this method we have always found that the products contain between 0.1% and 1% of organic residuals, which can often lead to undesirable immunological response on implantation.

According to the present invention we provide a process for the preparation of high purity bone mineral wherein the organic matter in degreased bone is degraded and solubilized by heating with ammonia or a primary amine, characterized in that the solubilized degradation products are extracted by washing with flowing water at temperatures below 60° C, such heating with primary amine and washing steps optionally being repeated, whereby substantially all organic matter removable by these steps is removed, the bone mineral so treated being heated in air at temperatures between 250° C. and 600° C.

Some earlier methods tried to extract the bone protein with hot ethylene diamine without water washing. This method is not very effective. Following the present invention the degreased bones are treated with hot amines (or acueous ammonia to degrade and solublize the originally insoluble proteins and the extraction of the solubilized degradation products takes place during washing with water.

We have found that this washing process is most important, since it not only causes the extraction of free soluble organics, but also the desorption of adsorbed degradation products. Due to the large specific surface of the bone mineral, adsorption is a very important effect preventing purification. Consequently washing with water has to be very extensive.

The final heating to sole hundred degrees centigrade brings about further desorption. At the same time, remaining organic contaminants are at least partially destroyed by oxidation.

Because bone mineral exists in an extremely fine crystalline state, it is not very stable and is subject to recrystallization. All operating conditions must be selected to avoid undue crystal growth.

Any vertebrate bone can be used as the starting material for the present process. Bovine femur is a preferred raw material. The bones must be free from other tissues, such as marrow, cartilage or periosteum. Cortical as well as cancellous bone may be used in the process yielding macroscopically different types of end product. The bones must be ground or cut into pieces. The shape and size of the particles are generally determined by the requirements of the end product. Since all treatments are largely diffusion-controlled, finer communication of the material facilitates the process.

The bones must substantially be completely degreased, since residual fats and their reaction products with amines will not readily be removed during the subsequent treatments. Degreasing is preferably performed by solvent extraction, suitable methods being known to those skilled in the art.

In general, degreasing can be effected by refluxing the bone material in the solvent which conveniently boils in the range 80° to 120° C., e.g. about 100° C. Suitable solvents include hydrocarbons such as toluene and methylcyclohexane.

Primary aliphatic or al cyclic amines are generally water soluble and are preferred as reagents for the protein degradation. These amines may possess more than one amino group per molecule and/or may contain other functional groups, e.g. hydroxyl groups. They preferably have 2 to 6 carbon atoms. Examples are cyclohexylamine, ethanolamine and ethylene diamine. Ammonia itself is also a suitable reagent. An addition of up to 50% water is often advantageous.

The degradation reaction may be performed by putting the degreased bone in a flask or vessel, adding enough reagent liquid to cover it and heating to a temperature between 80° C. and 200° C., preferably between 100° C. and 50° C. If ammonia or a low-boiling amine, such as ethylamine, is used, the reaction must be performed under pressure, preferably in an autoclave. Any more elaborate apparatus may also be used as long as the bone is in contact with hot reagent.

The duration of the heat treatment depends on the particle size of the bone, the reactivity of the amine and the reaction temperature, and may be between 2 and 200 hour. With bone pieces about 1 cm in diameter, using aqueous ethylene diamine as the reagent and a reaction temperature of 118° C., a reaction time of 50 hours gives very satisfactory results.

After the degradation reaction the reagent, which now already contains a proportion of the degradation products, is drained off. The treated bone is transferred to a rinsing bath. After removal of most of the residual reagent the velocity of the continuous water-flow is adjusted to between 1 and 50cm per hour, 10cm/hour being a preferred velocity. A faster water-flow may be used, but this may not accelerate the process. To avoid recrystallization, the water temperature should not exceed 60° C. The water temperature should not, however, be unduly low if efficient extraction is to be achieved and is preferably above 10° C. A temperature of approximately 20° C. is preferred. The presence of amines in the washing water can easily be detected by pH measurement. Even after complete elimination of the reagent amine, desorption of degradation products still takes place. The washing process is therefore continued for 5 to 25 days, the duration depending largely on the particle size of the bone.

To achieve particularly high purity, the amine treatment and the washing must be repeated. When relatively large pieces of cortical bone are processed, repetition of the treatment may be necessary.

The final and essential step in the treatment of the bone mineral consists of dry heating to temperatures between 250° C. and 600° C., preferably not greater than 550° C., more preferably between 350° C. and 500° C., for several hours. The higher temperatures are more effective in removing contaminants but tend to increase the risk of recrystallization with consequent increase of crystal size. Heating in an oxygen-enriched atmosphere promotes the beneficial oxidation of organic residues.

The bone mineral produced by the process of the invention is a white, chalky, brittle material, showing the macrosttucture of the original bone. On examination under the electron microscope, crystalline platelets no thicker than 100 Å units and 200 to 400 Å in diameter may be seen. By X-ray diffractography the presence of a hydroxylapatite lattice structure is confirmed. The width of the interferences is in agreement with the above-found crystal size. By mercury porosimetry a specific surface of $60m^2$ per g. has been measured.

The protein content is below the detection limit of the Lowry method (135opm) and the overall content of organic impurities 's certainly below 150 ppm. In contrast, repetition of the methods described in the above literature shows that the products in general contain substantial contents of organic impurities, normally above 1000ppm and often significantly more.

According to a further feature of the present invention we provide a bone mineral for use in medicine having substantially the crystal structure and mineral microstructure of natural bone permitting physiologically controlled, cell mediated remodelling on implantation, while having in organic impurity content below 150 parts per million. The bone mineral produced by the method of the invention shows, in fact, no organic impurities on electron microscopic examination at a magnification of 100,000.

In contrast to previously proposed natural or synthetic bone mineral materials, the product according to the invention is readily remodelled by the action of osteoclasts to effect resorption of bone mineral and the action of osteoblasts to produce new bone to eventually replace the implant.

The bone mineral according to the invention may thus be used as a remodelling implant or prosthetic bone replacement, for example in orthopedic surgery, including hip revisions, replacement of bone loss e.g. in traumatology, remodelling in maxillo facial surgery or filling periodontal defects and tooth extraction sockets. In this context, the bone mineral may have adsorbed or absorbed therein one or more physiologically active substances.

Physiologically active substances which may be adsorbed onto the bone mineral are preferably at least partially water-soluble and include antibacterial substances such as antibiotics, e.g. penicillins, cephalosporins, aminoglycosides etc., sulphonamides and, in particular, condensation products of formaldehyde with taurinamide or N-substituted taurinamide. The latter compounds may be represented by the formula

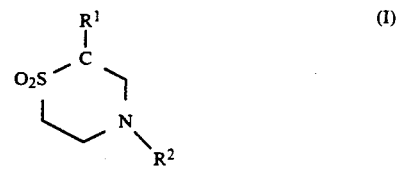
(I)

where $R^1$ is hydrogen or a $C_{1-4}$ alkyl group and $R^2$ is hydrogen or a group of the formula

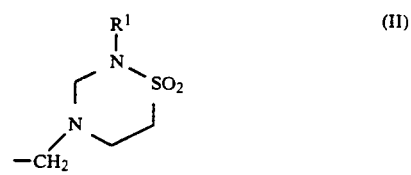
(II)

wherein R¹ has the above meaning.

The compound of formula(I) in which R¹ and R² are both hydrogen is taurultam while the compound in which R¹ is hydrogen and R² has the formula (II) is taurolidine. These compounds act as methylol transfer agents and are effective not only in destroying both gram negative and gram position bacteria but also in inactivating both endotoxins and exotoxins produced by the bacteria.

Other useful physiologically active substances include proteins and polypeptides capable of assisting bone regeneration especially non-collagenous proteins derived from bone matrix and bone cells. These include mitrognic factors such as skeletal growth factor and morphogenic and angiogenic factors as well as transforming growth factors, α and β types 1 and/or 2. Type 2 is especially important.

It has been found that while it is important in most instances to avoid significant modification of the size of the bone mineral crystallites, in order to ensure that the bone pieces when implanted, are readily converted into natural bone, there are certain environments, notably the highly vascularised maxillo facial region, where there may be some benefit in slight modification of the structure of the bone mineral to delay unduly rapid resorption. We have found that in this context it may be beneficial to increase the temperature of the final heating step to above 600° C., namely to a temperature between 600° and 700° C. Over this temperature range, there is modest increase in crystal platelet size and an increase in pore size. It is possible in this way to provide the surgeon with a range of bone mineral prosthetic products having different physical and physiological properties, by varying the temperature of the final heating step.

The following Examples are given by way of illustration only:

EXAMPLE 1

(a) Preparation of Degreased Bone

Femurs of freshly slaughtered rattle are sawed into slices 1 cm thick. These slices are cleaned by repeated boiling in water and by cutting off appending soft tissues. The material is dried at 100° C. in a circulating air even overnight.

Cortical and cancellous bone are processed separately. The cortical bone rings are cut into pieces 1 cm wide. The cancellous bone slices are sawed into plates 15 mm square.

The dried bone is transferred to a Soxhlet extractor modified for hot extraction and is extracted for 72 hours with boiling toluene The degreased bone can be stored after drying at 80° C. in closed containers.

(b) Preparation of Granular Bone Mineral 1700g degreased cortical bone, 1000 ml 99% ethylene diamine and 150 ml deionized water are heated under reflux in an Erlenmeyer flask immersed in an oil bath for a period of 50 hours. Boiling begins at 115° C. The temperature of the boiling mixture rises to 119° C. towards the end of the treatment.

After cooling, the reddish-brown amine reagent is decanted, and the bones re-rinsed three times with cold, deionized water.

The bone material is transferred to a glass cylinder fitted with a gritted glass support near the bottom. A continuous flow of water is passed through the porous glass disk and the layer of bone material.

The crude bone mineral is dried at 100° C. in a circulating air oven and ground on a roller mill to particle size below 2 mm.

The above-described amine treatment is repeated in exactly the same way using the pretreated material, but the subsequent washing is extended to 15 days.

The resulting bone mineral is dried at 160° C. and then heated to 350° C. in a porcelain pan for 20 hours.

1102g of white granular, pure bone mineral are obtained. The material can be separated by sieving into fractions of more uniform particle size.

EXAMPLE 2

Preparation of Cancellous Bone Mineral

Principally the same methods described in Example 1(b) are used. 600g degreased cancellous bone plates from Example 1(a), 1500 ml 1 99% ethylene diamine and 75 ml deionized water are heated under reflux for 50 hours. The treated bone is washed with water during 6 days.

The wet bone is subjected to a second similar treatment with 1500 ml ethylene diamine, an addition of water being omitted. The subsequent washing is prolonged to 17 days.

The final drying and heat treatment at 350° C. is performed in exactly the same way as described in Example 1(b). 366 g of pure, white, extremely friable, cancellous bone mineral are produced.

EXAMPLE 3

Preparation of Cortical Bone Mineral Pieces 1700g degreased cortical bone pieces are treated with ethylene diamine/water mixture as described in Example 1(b) and washed during 6 days.

The wet raw bone mineral is subjected to a second similar treatment using 1000ml ethylene diamine and 50 ml water, followed by a 10 day water washing.

To achieve highest purity, the wet bone mineral pieces are boiled 5 days in 1 liter pure ethylene diamine and then extracted in a slow stream (1 liter/hour) of cold deionized water for 22 days.

The product is finally dried overnight at 160° C. and then heated to 400° C. during 25 hours.

1085g of faintly reddish, brittle bone mineral pieces are yielded. Eventual organic contaminations could not be detected, their concentration being below the analytical detection limit.

EXAMPLE 4

Granular bone mineral with a particle size between 1 and 2 mm was prepared using the procedures described in Example 1. The material was characterized by electron microscopy, X-ray diffractography and mercury porosimetry. Each of these methods measures a different property of the material. Using electron microscopy it was found, that the material consists of crystalline platelets about 200 to 400 Å units in size (20 to 40nm).

Their thickness appear to be at most 100 Å units (10nm), since the crystals are still permeated by the electrons. The crystal size distribution seems to be rather narrow, but due to the insufficient disagglomeration a more quantitative evaluation was not feasible.

FIG. 1 is an electron micrograph of the bone mineral of the invention at a magnification of 100,000.

By X-ray diffractography it was found, that the material had pure hydroxyl apatite crystal structure. No interferences of other lattice structures was observed. Using the Laue-Scherrer relation the average crystal size in the 002-direction could be estimated to 315 Å units (31.5nm) with confidence limits of 276 and 362 Å units (27.6 and 36.2nm).

Mercury porosimetry up to a pressure of 1000 atm yielded the following figures:

| Pore Volume | 0.249 cm³/g |
|---|---|
| Inner Surface | 41.700 m²/g |
| Most Frequent Pore Diameter | 18 nm |

When the measurement was discontinued at 1000atm the pore volume still rose with pressure. This means, that the material contains pores with diameters below 150 Å units (15nm), that were not penetrated earlier. The pore volume and inner surface given above should therefore be considered as lower limits.

EXAMPLE 5

High Temperature Treatment

Samples of the described material were heated for 18 hours to temperatures between 600° C. and 800° C. in an electric furnace and were then analyzed in the same way as the original product. The results are summarized in Table 1 hereinafter.

With rising heating temperature the crystals and the pores grow larger while the inner surface shrinks.

After heating to 600° C. the small pores with diameters less than 15nm have disappeared in favor of larger pores.

After heating 650° C. a very wide crystal size distribution and two predominant pore sizes with diameters of 34nm and 130nm are observed.

Raising the temperature from 700° C. to 800° C. decreases the pore volume abruptly from 0.216cm3/g to 0.042cm3/g probably due to the commencement of sintering.

Heating in the above temperature range used causes crystal growth but no change in the crystal lattice structure. This could be independently confirmed by thermodiffractography: At about 650° C. the formerly broad interferences rapidly become sharp without changing their directions.

TABLE 1

MODIFICATION OF CRYSTAL SIZE AND POROSITY BY HEAT TREATMENT

| Sample heated 18 hrs. to | Electron Microscopy crystal size approx. (nm) | x-ray Diffractography | | | Mercury Porosimetry | | |
|---|---|---|---|---|---|---|---|
| | | crystal size 002 (mn) | confidence (nm) | limits (nm) | pore volume (cm³/g) | inner surface (m²g) | most frequent pore diameter (nm) |
| no heating | 10 × 20 × 40 | 31.5 | 27.6 | 36.2 | >0.249 | >41.7 | 18 |
| 600° C. | 10 × 30 × 60 | 30.7 | 27.6 | 33.9 | 0.318 | 36.3 | 32 |
| 650° C. | 20 to 250 | 47.7 | 41.6 | 54.4 | 0.282 | 17.7 | 34 + 130 |
| 700° C. | 100 to 300 | 59.6 | 58.9 | 689.9 | 0.216 | 5.2 | 160 |
| 800° C. | 100 to 400 | 61.2 | 52.0 | 69.9 | 0.042 | 1.1 | about 200 |

We claim:

1. A process for the preparation of high purity bone mineral wherein the organic matter in degreased bone is degraded and solubilized by heating with ammonia or a primary amine, characterized in that the solubilized degradation products are extracted by washing with flowing water at temperatures below 60° C., such heating with primary amine and washing steps optionally being repeated, whereby substantially all organic matter removable by these steps is removed so as to provide bone mineral having an organic impurity content less than 150 parts per million and a protein content less than 135 parts per million, the bone mineral so treated being heated in air at temperatures between 250° C. and 600° C.

2. A process as claimed in claim 1 in which the primary amine is an aliphatic or alicyclic amine having one or more primary amino groups.

3. A process as claimed in claim 1 or claim 2 in which the bone is heated with the primary amine or ammonia at a temperature in the range 100° to 150° C.

4. A process as claimed in claim 1 or claim 2 in which said flowing water flows at 1 to 50 cm per hour.

5. A process as claimed in claim 1 or claim 2 in which the final heating is in the range 350° to 500° C.

* * * * *

UNITED STATES PATENT AND TRADEMARK OFFICE
CERTIFICATE OF CORRECTION

PATENT NO.    : 5,167,961
DATED         : December 1, 1992
INVENTOR(S)   : Heinz Lussi, et al.

It is certified that error appears in the above-identified patent and that said Letters Patent is hereby corrected as shown below:

Column 2, line 9, delete "lia's[", and insert --liams--.

Column 2, line 19 change "residuals" to --residues--.

Column 2, line 48, change "sole" to --some--.

Column 2, bridging lines 65 and 66, delete "communication", and insert --comminution--.

Column 3, line 10, delete "al cyclic", and insert --alicyclic--.

Column 3, line 23, delete "50°", and insert --150°--.

UNITED STATES PATENT AND TRADEMARK OFFICE
CERTIFICATE OF CORRECTION

PATENT NO. : 5,167,961
DATED : December 1, 1992
INVENTOR(S) : Heinz Lussi, et al.

It is certified that error appears in the above-identified patent and that said Letters Patent is hereby corrected as shown below:

Column 3, line 31, delete "hour.", and insert --hours.--

Column 3, line 50, delete "desorption", and insert --desorbtion--.

Column 4, line 10, delete "135opm", and insert --135 ppm--.

Column 4, line 34, delete "orthopedic", and insert --orthopaedic--.

Column 4, Formula 1, change the "C" to an --N--.

Column 5, line 14, change "mitrognic" to --mitogenic--.

Column 5, line 42, change "rattle" to --cattle--.

Column 5, line 46, change "even" to --oven--.

Column 5, line 68, change "gritted" to --fritted--.

UNITED STATES PATENT AND TRADEMARK OFFICE
CERTIFICATE OF CORRECTION

PATENT NO. : 5,167,961

DATED : December 1, 1992

INVENTOR(S) : Heinz Lussi, et al.

It is certified that error appears in the above-identified patent and that said Letters Patent is hereby corrected as shown below:

Column 6, line 30, start a new paragraph beginning with "366 g".

Column 6, line 43, change "liter" to --litre--.

Column 8, Table 1, line 9, change "58.9" to --48.9-- and change "689.9" to --69.9--.

Signed and Sealed this

Fourteenth Day of December, 1993

BRUCE LEHMAN

*Commissioner of Patents and Trademarks*